(12) United States Patent
Sato (10) Patent No.: US 10,314,494 B2
(45) Date of Patent: Jun. 11, 2019

(54) OBJECT INFORMATION ACQUIRING APPARATUS AND METHOD OF CONTROLLING OBJECT INFORMATION ACQUIRING APPARATUS

(71) Applicant: CANON KABUSHIKI KAISHA, Tokyo (JP)

(72) Inventor: Akira Sato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 257 days.

(21) Appl. No.: 14/049,354

(22) Filed: Oct. 9, 2013

(65) Prior Publication Data
US 2014/0114169 A1    Apr. 24, 2014

(30) Foreign Application Priority Data

Oct. 18, 2012    (JP) .................................. 2012-230618

(51) Int. Cl.
*A61B 5/00*    (2006.01)
(52) U.S. Cl.
CPC .................................. *A61B 5/0095* (2013.01)
(58) Field of Classification Search
CPC ......... A61B 5/0095; H01S 5/068–0687; H01S 3/137; H01S 5/06206; H01S 5/0622; H01S 3/10084; H01S 3/10092; H01S 5/06255; H01S 5/06256; H01S 5/06258; H01S 5/141; H01S 5/142; H01S 5/143
See application file for complete search history.

(56) References Cited

U.S. PATENT DOCUMENTS

| | | | |
|---|---|---|---|
| 5,840,023 A | 11/1998 | Oraevsky et al. | 600/407 |
| 5,941,821 A * | 8/1999 | Chou | A61B 5/0095 374/45 |
| 6,501,774 B2 * | 12/2002 | Kuwahara | H01S 5/06804 372/29.02 |
| 6,602,186 B1 * | 8/2003 | Sugimoto | A61B 1/00009 600/126 |

(Continued)

FOREIGN PATENT DOCUMENTS

WO    WO 2012/120885 A    9/2012

OTHER PUBLICATIONS

S.A. Ermilov et al., "Development of Laser Optoacoustic and Ultrasonic Imaging System for Breast Cancer Utilizing Handheld Array Probes", *Proc. of SPIE*, vol. 7177 (2009).

*Primary Examiner* — Pascal M Bui Pho
*Assistant Examiner* — Colin T. Sakamoto
(74) *Attorney, Agent, or Firm* — Venable LLP (57) ABSTRACT

An object information acquiring apparatus applying light to an object, receiving an acoustic wave generated inside the object, and acquiring information on an inside of the object on the basis of the acoustic wave comprises a light source configured to selectively emit irradiation light with at least two kinds of wavelengths; a wavelength switching unit for instructing the light source to implement switching between the wavelengths of the irradiation light; an illumination optical system guiding the irradiation light to the object; and a light irradiation limiting unit for limiting irradiation of the light to the object during a period from when the wavelength switching unit provides an instruction on wavelength switching of the light to when the light source completes the wavelength switching of the light.

15 Claims, 8 Drawing Sheets

(56) References Cited

U.S. PATENT DOCUMENTS

| | | | |
|---|---|---|---|
| 2011/0306865 A1* | 12/2011 | Thornton | A61B 5/0059 600/407 |
| 2012/0238858 A1* | 9/2012 | Tokita | A61B 5/0091 600/407 |
| 2013/0039147 A1* | 2/2013 | Witte | A61B 5/0093 367/7 |
| 2014/0005556 A1 | 1/2014 | Hirota et al. | 600/476 |
| 2014/0187902 A1 | 7/2014 | Sato et al. | 600/407 |

* cited by examiner

OBJECT INFORMATION ACQUIRING APPARATUS AND METHOD OF CONTROLLING OBJECT INFORMATION ACQUIRING APPARATUS

BACKGROUND OF THE INVENTION

Field of the Invention

The present invention relates to a technology for observing the constituents or the shape of the surface and the inside of an object.

Description of the Related Art

A technology of irradiating a biological body with a laser beam to generate an ultrasonic wave (photoacoustic wave) resulting from laser irradiation inside the biological body, and analyzing the photoacoustic wave to analyze the structure or the state of the surface and the inside of the biological body has been devised (U.S. Pat. No. 5,840,023).

This is also referred to as photoacoustic wave measurement, and since an examination is noninvasively performed, there are movements to divert the photoacoustic wave measurement for medical use in order to perform the examination of the inside of a human body.

Additionally, X-ray mammography for the purpose of the examination and the diagnosis of breast cancer is known, and a manual scanning photoacoustic measurement apparatuses have been developed for the purpose of breast cancer examination (S. A. Ermilov et al., Development of laser optoacoustic and ultrasonic imaging system for breast cancer utilizing handheld array probes, Photons Plus Ultrasound: Imaging and Sensing 2009, Proc. of SPIE, vol. 7177, 2009).

The photoacoustic measurement apparatus can acquire various pieces of information on the inside of an object by the wavelength of light applied to the object (hereinafter, irradiation light). For example, when near-infrared light that has a property of being likely to be absorbed in hemoglobin in blood is used, a blood vessel image can be acquired. Additionally, the oxygen saturation in blood can be measured by performing measurement a plurality of times by using irradiation light with a wavelength that is likely to be absorbed in oxygenated hemoglobin, and irradiation light with a wavelength that is likely to be absorbed in reduced hemoglobin, and comparing a plurality of blood vessel images that are acquired.

In a case where the measurement is performed a plurality of times while changing the wavelength of irradiation light, when the positions of ultrasound probe with respect to a measurement segment are different, the acquired images are displaced, so that the comparison cannot be correctly performed. Accordingly, the positions of the ultrasound probe with respect to an object are desirably the same in all of the measurement.

In the manual scanning photoacoustic measurement apparatus, since an illumination optical system, an irradiation port, and an ultrasound probe are housed in a single probe, the relative positions of the irradiation port and the ultrasound probe are fixed. However, it is difficult to manually reproduce the angle of the probe with respect to the object, pressing force each time the measurement is performed.

Therefore, in a case where a plurality of pieces of photoacoustic data are acquired to be compared, measurement is preferably performed a plurality of times at a time in a state where the probe is pressed against the object and maintains the posture, while changing the wavelength of the irradiation light.

However, a certain amount of time is required to switch the wavelength of the irradiation light. Therefore, the conventional photoacoustic measurement apparatus has a problem that unnecessary irradiation light which is not used in measurement is applied to an object when the wavelengths are switched, so that an unwanted physical burden is imposed on an object.

SUMMARY OF THE INVENTION

The present invention has been conceived in order to solve the aforementioned problems, and the purpose thereof is to provide a technique of suppressing irradiation of unnecessary irradiation light resulting from the switching of wavelength in an object information acquiring apparatus for performing photoacoustic measurement at a plurality of wavelengths.

The present invention in its one aspect provides an object information acquiring apparatus applying light to an object, receiving an acoustic wave generated inside the object by an acoustic wave probe, and acquiring information on an inside of the object on the basis of the acoustic wave, comprising a light source configured to selectively emit irradiation light with at least two kinds of wavelengths, which is applied to the object; a wavelength switching unit for instructing the light source to implement switching between the wavelengths of the irradiation light; an illumination optical system connected to the light source, and guiding the irradiation light to the object; and a light irradiation limiting unit for limiting irradiation of the irradiation light to the object during a period from when the wavelength switching unit provides an instruction on wavelength switching of the irradiation light to the light source to when the light source completes the wavelength switching of the irradiation light.

The present invention in its another aspect provides a method of controlling an object information acquiring apparatus applying light to an object, receiving an acoustic wave generated inside the object by an acoustic wave probe, and acquiring information on an inside of the object on the basis of the acoustic wave, comprising a first light irradiation step of generating irradiation light with a first wavelength to be applied to the object and applying the irradiation light to the object through an illumination optical system; a light irradiation limiting step of limiting the irradiation of the irradiation light to the object before implement switching between wavelengths of the irradiation light; a wavelength change step of changing the wavelength of the irradiation light applied to the object into a second wavelength that is different from the first wavelength; a light irradiation limitation release step of releasing the irradiation limitation of the irradiation light to the object after completing the switching of the wavelength of the irradiation light; and a second light irradiation step of applying the irradiation light with the second wavelength to the object through the illumination optical system.

According to the present invention, it is possible to provide a technique of suppressing irradiation of unnecessary irradiation light resulting from the switching of the wavelength in an object information acquiring apparatus for performing photoacoustic measurement at a plurality of wavelengths.

Further features of the present invention will become apparent from the following description of exemplary embodiments with reference to the attached drawings.

DESCRIPTION OF THE EMBODIMENTS

Hereinafter, embodiments of the present invention will be described in detail with reference to the drawings. Note that the same components are generally denoted by the same reference numerals, and the description thereof will be omitted.

(First Embodiment)

<System Configuration>

Figure 1:
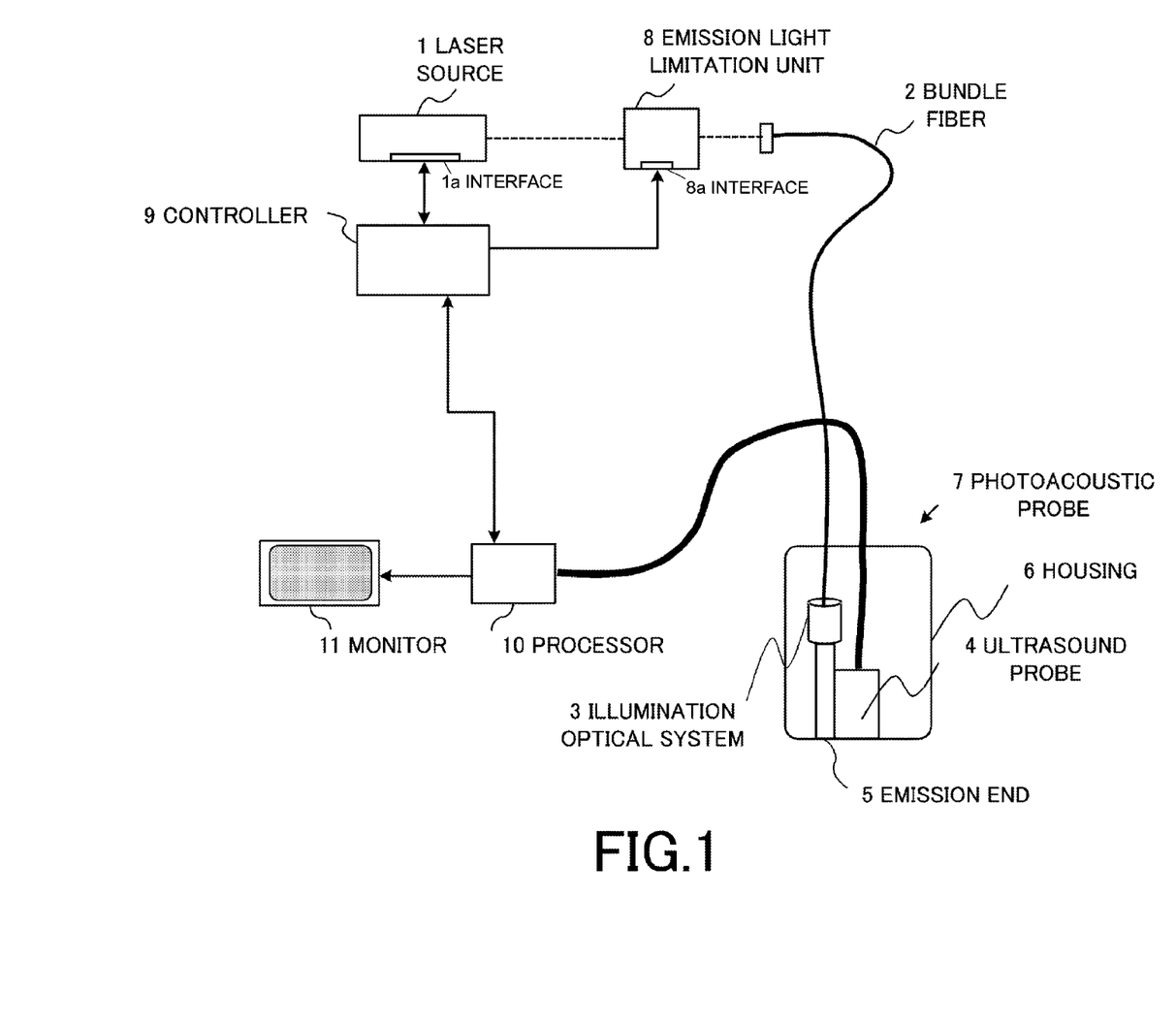
FIG. 1 is a configuration diagram of a photoacoustic measurement apparatus according to a first embodiment.

A configuration of a photoacoustic measurement apparatus according to a first embodiment will be now described with reference to FIG. 1. The photoacoustic measurement apparatus according to the first embodiment of the present invention is a manual scanning photoacoustic imaging apparatus for imaging the information of a biological body being an object in order to diagnose a malignant tumor, a vascular disease, or the like, or observe the progress of chemical treatment or the like. The information of the biological body is a generation source distribution of acoustic waves generated by light irradiation, an initial sound pressure distribution inside the biological body, or an optical energy absorption density distribution derived from the initial sound pressure distribution.

The photoacoustic measurement apparatus according to the first embodiment of the present invention includes a laser source 1, a bundle fiber 2, a photoacoustic probe 7, an emission light limitation unit 8, a controller 9, a processor 10, and a monitor 11. Hereinafter, while each of unit configuring the photoacoustic measurement apparatus according to the first embodiment is described, an outline of a method of measuring an object will be described.

<<Laser Source 1>>

The laser source 1 is a unit for generating near-infrared rays applied to a biological body being an object.

From the laser source 1, light with a specific wavelength that is absorbed in a specific constituent among constituents that configure a biological body is preferably generated. Specifically, a pulse light source capable of generating pulsed light of several nanoseconds order to several hundred nanoseconds order is preferable. The light source preferably is a light source that generates a laser beam, but a light emission diode or the like can be used in place of the laser source. In a case of a laser is used, various lasers such as a solid-state laser, a gas laser, a dye laser and a semiconductor laser can be used.

The laser source 1 is a "light source" in the present invention, and light generated by the laser source 1 (hereinafter, laser beam) is "irradiation light" in the present invention.

In this embodiment, a single light source is used. However, a plurality of light sources may be used. In a case where a plurality of light sources are used, a plurality of light sources that oscillate the same wavelength may be used in order to increase the irradiation intensity of light applied to a biological body, or a plurality of light sources that oscillate different wavelengths may be used in order to measure the difference in wavelengths of an optical properties distribution. If an OPO (Optical Parametric Oscillator) or dye capable of changing an oscillating wavelength is used as the light source, the difference in wavelengths of the optical properties distribution can be measured.

The range of the wavelength of a laser beam is preferably 700 nm to 1100 nm of less absorption in a biological body. However, in a case where an optical properties distribution of biological body tissues relatively around the surface of the biological body is obtained, a wavelength range wider than the aforementioned wavelength range, for example, a wavelength range of 400 nm to 1600 nm can be also used. Among light of the aforementioned range, a specific wavelength may be selected based on a constituent to be measured.

The irradiation frequency of the laser source is generally decided. This is set as a design value in order to continuously apply pulsed light with a desired intensity. Since the irradiation frequency affects the number of photoacoustic measurements that can be performed per unit time, a higher irradiation frequency is preferable. In this embodiment, the irradiation frequency of the laser source is decided as 10 Hz.

Furthermore, the laser source 1 according to this embodiment has a wavelength varying mechanism, and can change the wavelength of a generated laser beam. Specifically, a birefringent filter, a prism, or the like arranged on an optical path of a laser beam is rotated by driving unit such as a stepping motor, so that light with a required wavelength is taken out to be emitted.

Additionally, the laser source 1 includes an interface 1a for instructing the wavelength of the generated laser beam from outside. In a case where the wavelengths of generated light are two in number, a signal transmitted/received by the interface may be a binary signal (i.e. 0, 1), or may be an interactive signal configured by a command and a response.

The laser source 1 preferably includes a unit for detecting the completion of wavelength change, and an interface 1a for notifying the outside that the change of the wavelength is completed. For example, when the change of the wavelength is instructed, the angle of the aforementioned prism is acquired, so that the wavelength of an emitted laser beam is acquired. When the change to the designated wavelength is completed, it is notified to the outside that the change of the wavelength is completed, through the interface 1a. However, when time required for the wavelength change can be previously predicted, the interface for notifying the outside of the status is not always required.

In this embodiment, the laser source 1 has the wavelength varying mechanism. However, the wavelength varying mechanism may be an apparatus separate from the laser source 1. Alternatively, a plurality of light sources that emit laser beams with different wavelengths may be switched. As long as laser beams with a plurality of wavelengths can be selectively emitted, any laser source can be employed. The method of changing the wavelength of a laser beam, and the method of detecting the completion of the wavelength change, which are described above, are only examples, and the embodiments of the present invention are not limited to these.

The light emitted by the laser source 1 is guided to the photoacoustic probe 7 by the connected bundle fiber 2.

<<Bundle Fiber 2>>

The bundle fiber 2 is the aggregate of optical fibers for guiding, to the photoacoustic probe 7, a laser beam generated by the light source. In this embodiment, the bundle fiber is used for the transmission of a laser beam. However, the transmission of a laser beam may be performed by combination of a light shielding tube and a reflection mirror. As long as a laser beam emitted by the light source can be guided to the photoacoustic probe, any component may be used.

A configuration of the photoacoustic probe 7 will be now described. The photoacoustic probe 7 includes a housing 6, an illumination optical system 3 housed in the housing 6, and an ultrasound probe 4. The housing 6 is provided with an emission end 5 that is an opening serving as an exit of a laser beam.

<<Illumination Optical System 3>>

The illumination optical system 3 is a unit for performing beam forming of an incident laser beam. Specifically, the illumination optical system 3 is an optical member that is configured by a lens, a diffuser panel, and the like such that a desired beam shape, and a light intensity distribution are obtained. In this embodiment, the illumination optical system 3 is configured by an enlarging optical system for expanding an illumination range, and a diffuser panel for preventing a rapid laser intensity distribution. The "illumination optical system" in the present invention indicates all units for guiding a laser beam generated from the light source to the surface of an object, and includes both of the bundle fiber 2 through which the laser beam passes, and the illumination optical system 3, in this embodiment.

In this embodiment, the illumination optical system is arranged inside the photoacoustic probe 7. However, the illumination optical system may be arranged on the light source side with respect to the bundle fiber 2, or the illumination optical systems may be arranged at a plurality of locations to perform a beam forming step at a the plurality of locations.

The formed laser beam is emitted from the emission end 5 that is an opening and is provided in the housing 6, and is applied to the object.

When the applied laser beam diffuses inside the object, and a part of the energy of light propagated inside the object is absorbed in a light absorber such as a blood vessel, an acoustic wave is generated from the light absorber by thermal expansion. That is, the laser beam is absorbed, so that the temperature of the light absorber is increased. As a result, the volume is increased, and an acoustic wave is generated. This phenomenon is referred to as a photoacoustic effect. The acoustic wave is typically an ultrasonic wave, and includes acoustic waves referred to as a sound wave, an ultrasonic wave, a photoacoustic wave, and a light-induced ultrasound wave.

<<Ultrasound Probe 4>>

The ultrasound probe 4 is a unit for detecting an acoustic wave generated or reflected inside a biological body being an object to convert the acoustic wave into an analog electric signal. The acoustic wave generated from the biological body is an ultrasonic wave of 100 KHz to 100 MHz, and therefore an ultrasonic wave detector capable of receiving the aforementioned frequency band is used for the ultrasound probe 4. Specifically, the examples thereof include a transducer using a piezoelectric phenomenon, a transducer using the resonance of light, or a transducer using change in a capacity. As long as the detector can detect an acoustic wave signal, any detector may be employed.

The electric signal converted by the ultrasound probe 4 is converted into image data by the processor 10. The photoacoustic wave is acquired and analyzed as described above, so that object information can be visualized. The object information that is a subject to be visualized is a generation source distribution of photoacoustic waves inside an object, or an initial sound pressure distribution of the inside of an object, an optical energy absorption density distribution derived from the initial sound pressure distribution, a light absorption coefficient distribution, or a concentration distribution of substances configuring tissues.

The examples of the concentration distribution of substances include an oxygen saturation distribution, and an oxygenated/reduced hemoglobin concentration distribution, for example. In this embodiment, measurement is performed a plurality of times while changing the wavelength of a laser beam, and image data is generated from a plurality of pieces of the acquired measurement data. The generated image data is displayed on the monitor 11 to be presented to a user.

<<Emission Light Limitation Unit 8>>

The photoacoustic measurement apparatus according to this embodiment further has the emission light limitation unit 8 in addition to the aforementioned configuration. The emission light limitation unit 8 is a light-shielding mechanism for shielding a laser beam, which is arranged between the laser source 1 and the bundle fiber 2, and light irradiation limiting unit in the present invention. In the first embodiment, a light shielding plate arranged on an optical path is driven and the optical path is closed and opened, thereby shielding a laser beam applied to an object.

The emission light limitation unt 8 includes an interface 8a for receiving an instruction on irradiation limitation from the outside. A signal received by the interface may be a binary signale )i.e. 0, 1) that represents "without irradiation limitation" and "with irradiation limitation", for example.

In the first embodiment, the emission light limitation unit 8 is arranged in front of the bundle fiber 2. However, it is merely required that the emiision light limitation unit is arranged on the illumination optical system in the present invention. For example, the emission light limitation unit may be incorporated in the laser source 1, or may be incorporated in the illumination optical system 3.

<<Controller 9>>

The controller 9 is a unit for controlling the laser source 1, and instructing the emission light limitation unit 8 about the presence or absence of irradiation limitation of a laser beam with respect to an object. The controller 9 is wavelength switching unit in the present invention. Specific processes will be described later.

<Irradiation Processes of Laser Beam>

Figure 2:
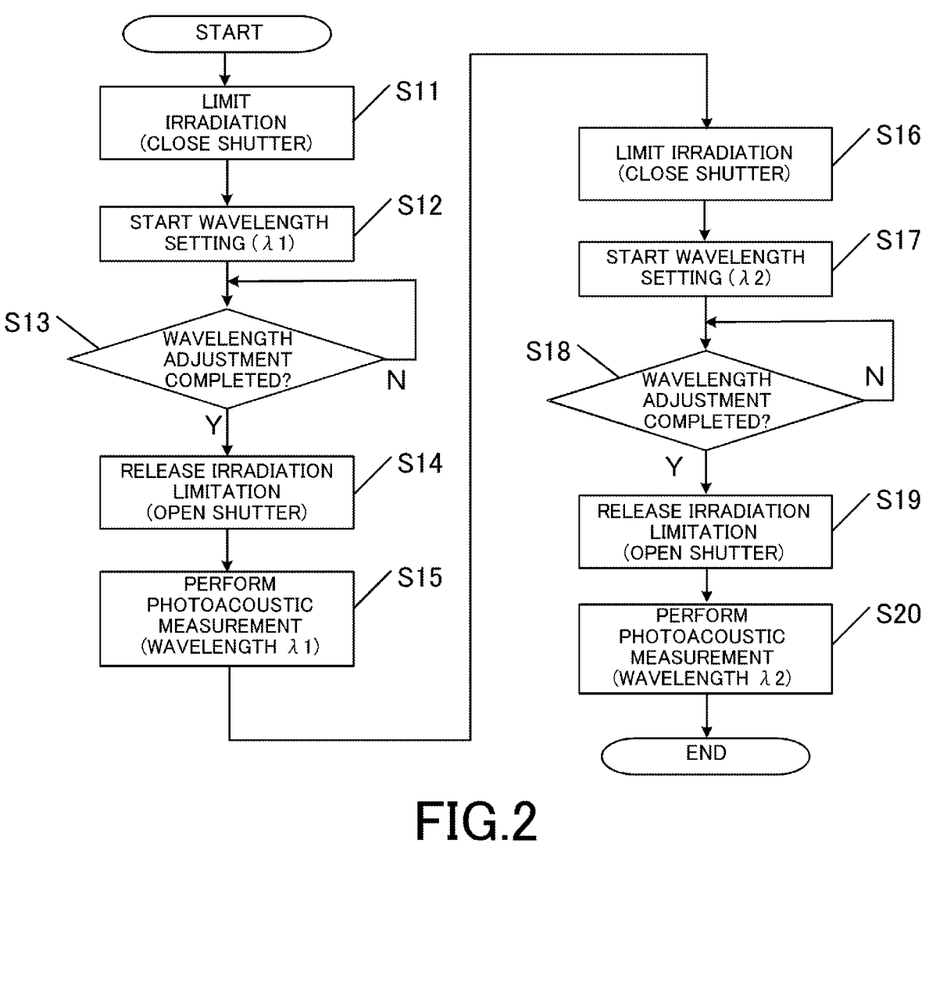
FIG. 2 is a process flowchart of the photoacoustic measurement apparatus according to the first embodiment.

Hereinafter, laser beam irradiation processes performed by the photoacoustic measurement apparatus according to this embodiment will be described with reference to a flowchart shown in FIG. 2. In this embodiment, a laser beam with a wavelength λ1, and a laser beam with a wavelength λ2 are applied in two processes. However, as long as the wavelengths of a laser beam to be used are two or more kinds, any number of kinds of the wavelengths may be employed. When the measurement is started, processes shown in FIG. 2 are started.

First, in Step S11, the controller 9 issues, to the emission light limitation unit 8, an instruction for closing a shutter. Consequently, the optical path of a laser beam is closed, so that the laser beam is not applied to an object.

Next, in Step S12, the controller 9 issues, to the laser source 1, an instruction for setting the wavelength of a laser beam to λ1 that is a first wavelength.

Step S13 is a step of waiting until the laser source 1 completes the setting of the wavelength. When the setting of the wavelength is completed, the laser source 1 notifies the controller 9 of the completion of the setting. For example, the laser source 1 notifies that the angle of the prism used for the change of the wavelength reaches a prescribed value, so that the controller 9 can know the completion of the setting of the wavelength. When the setting is not terminated, the controller 9 waits. When the setting is terminated, the process advances to Step S14.

In Step S14, the controller 9 issues, to the emission light limitation unit 8, an instruction for opening the shutter. Consequently, the optical path of the laser beam is opened, and irradiation of the laser beam to the object starts.

In Step S15, the controller 9 and the processor 10 perform photoacoustic measurement by using the laser beam with the wavelength λ1. Step S15 is a first light irradiation step in the present invention. When the measurement is terminated, the process advances to Step S16, and the controller 9 issues, to the emission light limitation unit 8, an instruction for closing the shutter. Consequently, the optical path of the laser beam is closed, and the irradiation of the laser beam to the object stops. Step S16 is a light irradiation limiting step in the present invention.

In Step S17, the controller 9 issues, to the laser source 1, an instruction for setting the wavelength of a laser beam to λ2 that is a second wavelength.

Step S18 is a step of waiting until the laser source 1 completes the setting of the wavelength. Similarly to Step S12, when the setting of the wavelength is completed, the laser source 1 notifies the controller 9 of the completion of the setting. When the setting is not terminated, the controller 9 waits. When the setting is completed, the process advances to Step S19. Step S17 and Step S18 are a wavelength change step in the present invention.

In Step S19, the controller 9 issues, to the emission light limitation unit 8, an instruction for opening the shutter. Consequently, the optical path of the laser beam is opened, and irradiation of the laser beam to the object starts. Step S19 is a light irradiation limitation release step in the present invention.

In Step S20, the controller 9 and the processor 10 perform photoacoustic measurement by using the laser beam of the wavelength λ2. A photoacoustic signal acquired in Step S15 and Step S20 is imaged by the processor 10 to be displayed on the monitor 11. Step S20 is a second light irradiation step in the present invention.

Figure 3:
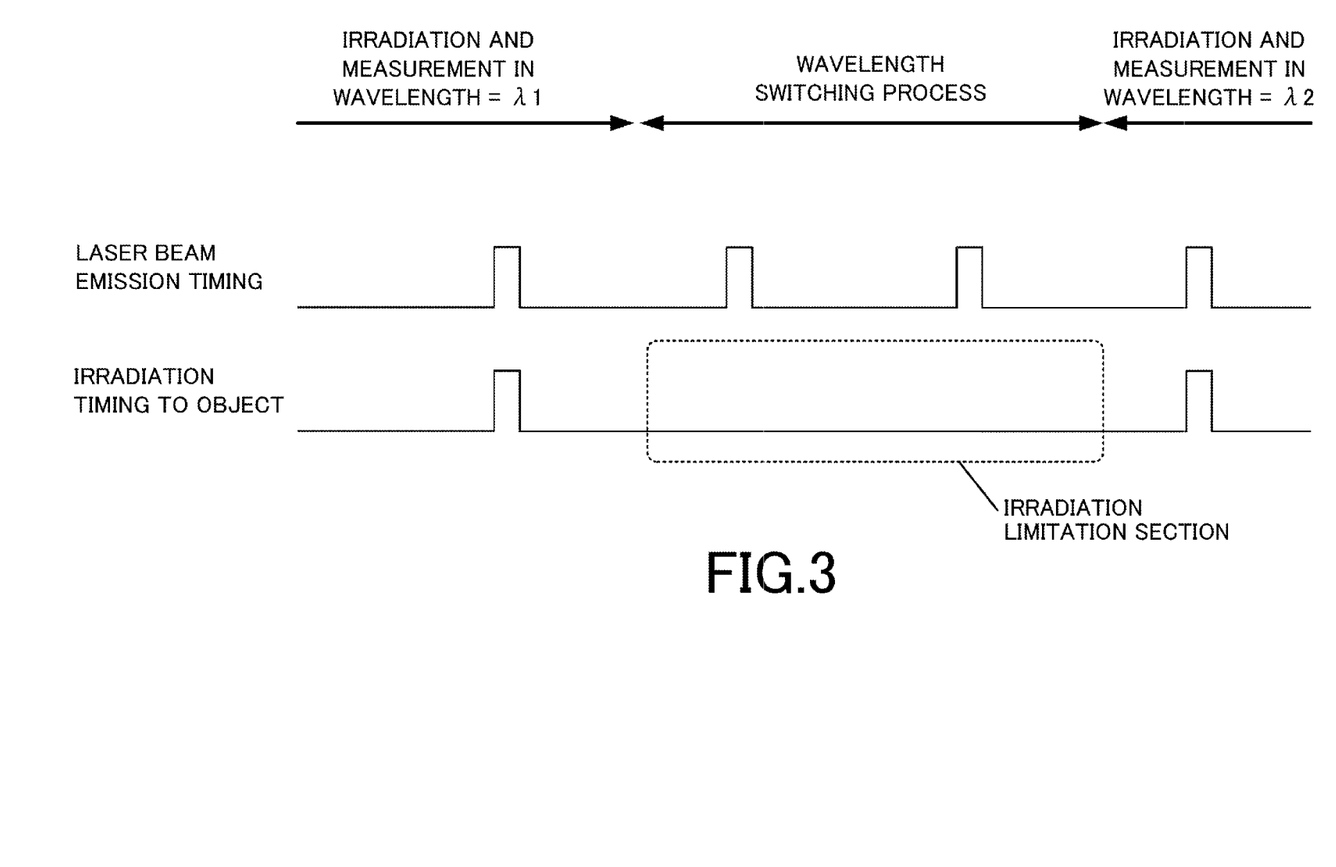
FIG. 3 is a figure representing the emission timing and the irradiation timing of a laser beam.

FIG. 3 is a figure for representing the emission timing of the laser beams and the irradiation timing to the object in a case where the aforementioned control is performed. When the process of setting (switching) the wavelength is started, the emission light limitation unit 8 limits the irradiation of the laser beam to the object until the switching is completed. In this example, a section surrounded by a dotted line is a section where the wavelength is set, and two pulses included in the section are not applied.

As described above, in the photoacoustic measurement apparatus according to this embodiment, the controller 9 detects the timing for suppressing the irradiation of the laser beam, and closes and opens the optical path of the laser beam. Consequently, the irradiation of an unnecessary laser beam to the object can be suppressed, and a physical burden of the object can be reduced.

This embodiment is particularly preferable for a photoacoustic measurement apparatus for manually scanning. Conventionally, a photoacoustic probe needs to be applied to an object again in order to prevent unnecessary laser beam irradiation resulting from the switching of the wavelength, which results in displacement. However, a mechanism for suppressing the irradiation of a laser beam is employed, so that this problem can be solved.

The closing of the optical path is performed by physical components, and hence next measurement can start immediately after the wavelength of a laser beam is changed, and the total measurement time can be shortened.

Figure 4A:
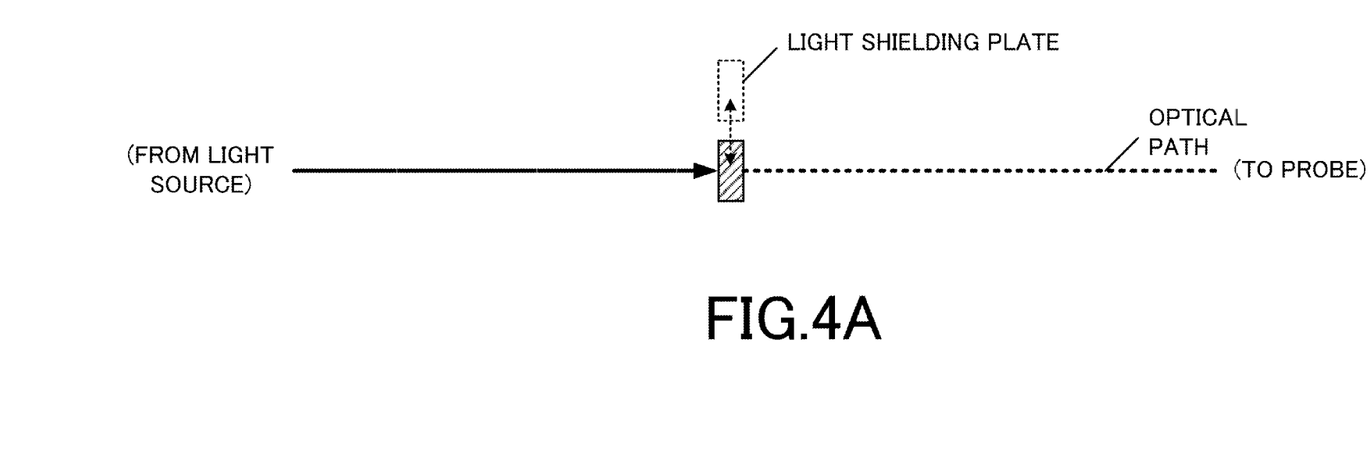
FIGS. 4A and 4B each are a figure for illustrating an irradiation limitation method of a laser beam in the first embodiment.
Figure 4B:
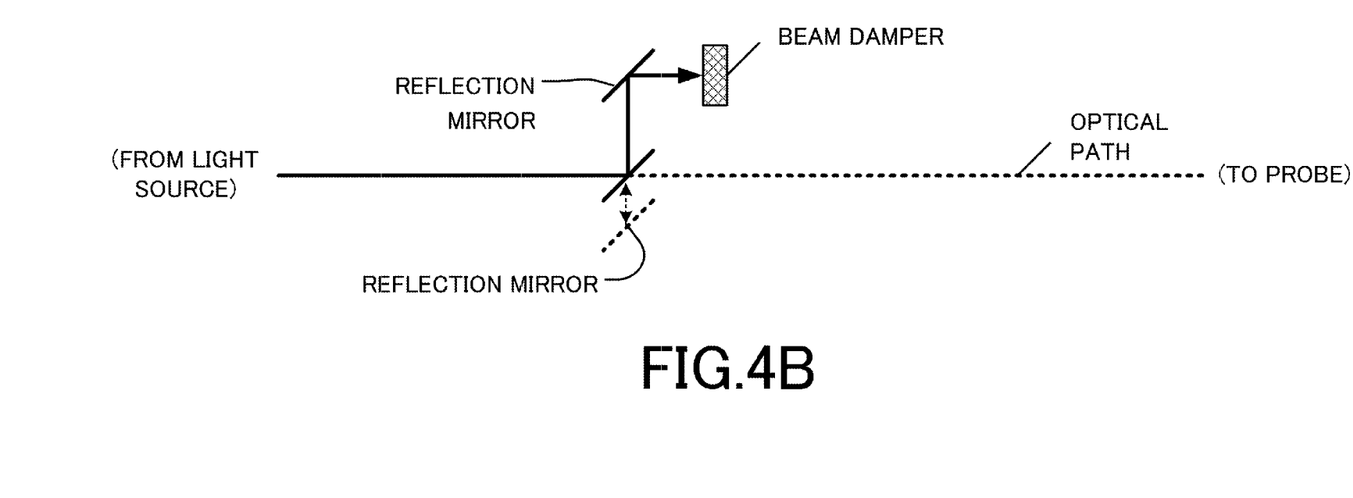

In the first embodiment, as in FIG. 4A, the light shielding plate is moved onto the optical path of a laser beam, so that the irradiation of the laser beam to the object is limited. However, as long as the laser beam can reach the light shielding plate, the light shielding plate maybe arranged and driven in any manner. For example, as in FIG. 4B, a method of guiding a laser beam to a beam damper by driving a mirror or a prism for reflecting the laser beam may be employed.

In this embodiment, irradiation limitation is performed both when the wavelength of the laser beam is set to λ1 and when the wavelength of the laser beam is set to λ2. However, as long as the irradiation of a laser beam unnecessary for measurement to an object can be prevented, the timing of the irradiation limitation is not limited to the exemplified timing.

(Second Embodiment)

A second embodiment is an embodiment where an emission light limitation unit 8 limits the irradiation of a laser beam to an object by using an optical member for attenuating light like a neutral density (ND) filter in place of the light shielding plate. A system configuration diagram and a process flowchart of a photoacoustic measurement apparatus of the second embodiment are similar to those of the first embodiment.

In the second embodiment, when the emission light limitation unit 8 receives, from a controller 9, an instruction for performing irradiation limitation, the ND filter is moved onto an optical path with motor drive, thereby attenuating the energy of a laser beam that passes. Specifically, in Step S11 and Step S16, the ND filter is moved onto the optical path, so that irradiation limitation is performed. Additionally, in Step S14 and Step S19, the ND filter is retreated from on the optical path, so that the irradiation limitation is released.

In this embodiment, the filter is used in place of the light shielding plate, and therefore the laser beam applied to the object cannot be shielded completely. However, a filter capable of sufficiently attenuating the energy of the laser beam is selected, so that the purpose of the invention that is to reduce a burden of a subject can be achieved.

Figure 5A:
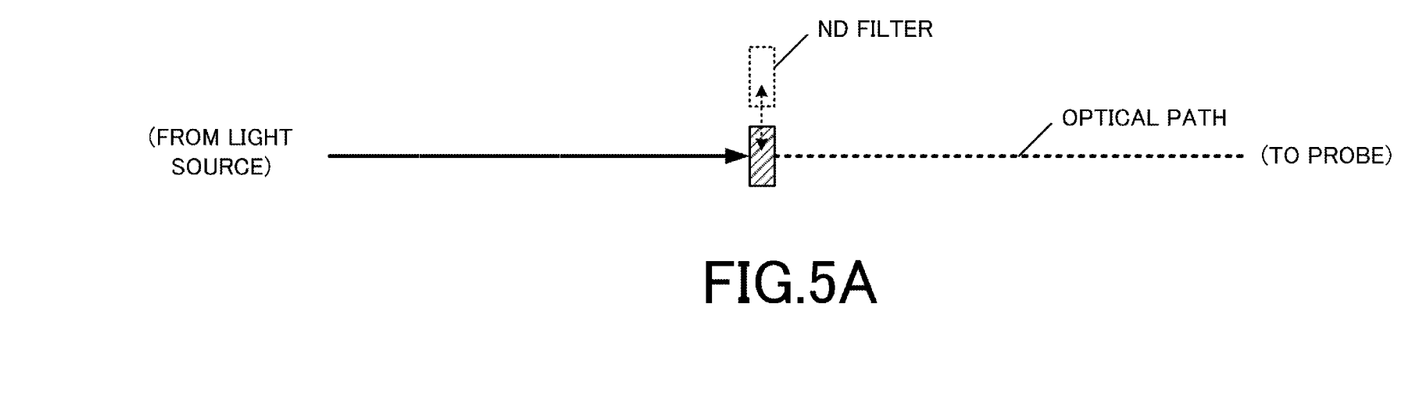
FIGS. 5A and 5B each are a figure for illustrating an irradiation limitation method of a laser beam in a second embodiment.
Figure 5B:
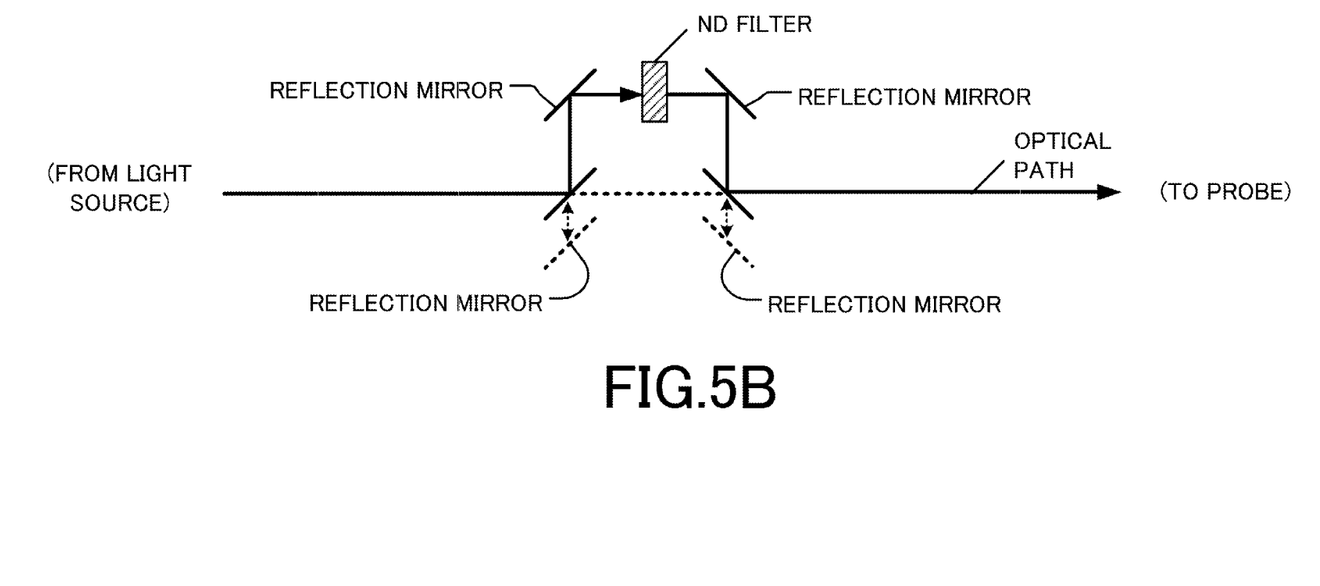

As long as a laser beam can pass through the ND filter, the filter may be arranged and driven in any manner. For example, as in FIG. 5A, the ND filter may be moved onto the optical path of the laser beam, or as in FIG. 5B, the optical path may be switched such that the laser beam passes through the ND filter.

Thus, as long as the light-shielding mechanism, which the emission light limitation unit 8 uses, attenuates the energy of a laser beam applied to an object, a light-shielding mechanism that does not completely shield the laser beam may be employed.

(Third Embodiment)

A third embodiment is an embodiment where an emission light limitation unit 8 limits the irradiation of a laser beam to an object by using an optical member for diffusing light. Irradiation light is diffused by using a diffusion lens in this example, but other optical member such as a diffuser panel may be used. A system configuration diagram and a process flowchart of a photoacoustic measurement apparatus of the third embodiment are similar to those of the first embodiment.

In the third embodiment, when the emission light limitation unit 8 receives, from a controller 9, an instruction for performing irradiation limitation, the diffusion lens is moved onto an optical path with motor drive, thereby diffusing a laser beam. Specifically, in Step S11 and Step S16, the diffusion lens is moved onto the optical path, so that irradiation limitation is performed. Additionally, in Step S14 and Step S19, the diffusion lens is retreated from on the optical path, so that the irradiation limitation is released.

In this embodiment, the laser beam applied to the object cannot be shielded completely similarly to the second embodiment. However, an optical member capable of sufficiently diffusing the energy of the laser beam is selected, so that the purpose of the invention that is to reduce a burden of a subject can be achieved.

As long as the laser beam can reach an optical member such as a diffusion lens and a diffuser panel, the optical member may be arranged and driven in any manner. For example, similarly to the examples shown in FIGS. 5A and 5B, the diffusion lens or the diffuser panel may be moved onto an optical path, or the optical path maybe switched such that the laser beam passes through the diffusion lens or the diffuser panel.

(Fourth Embodiment)

Figure 6:
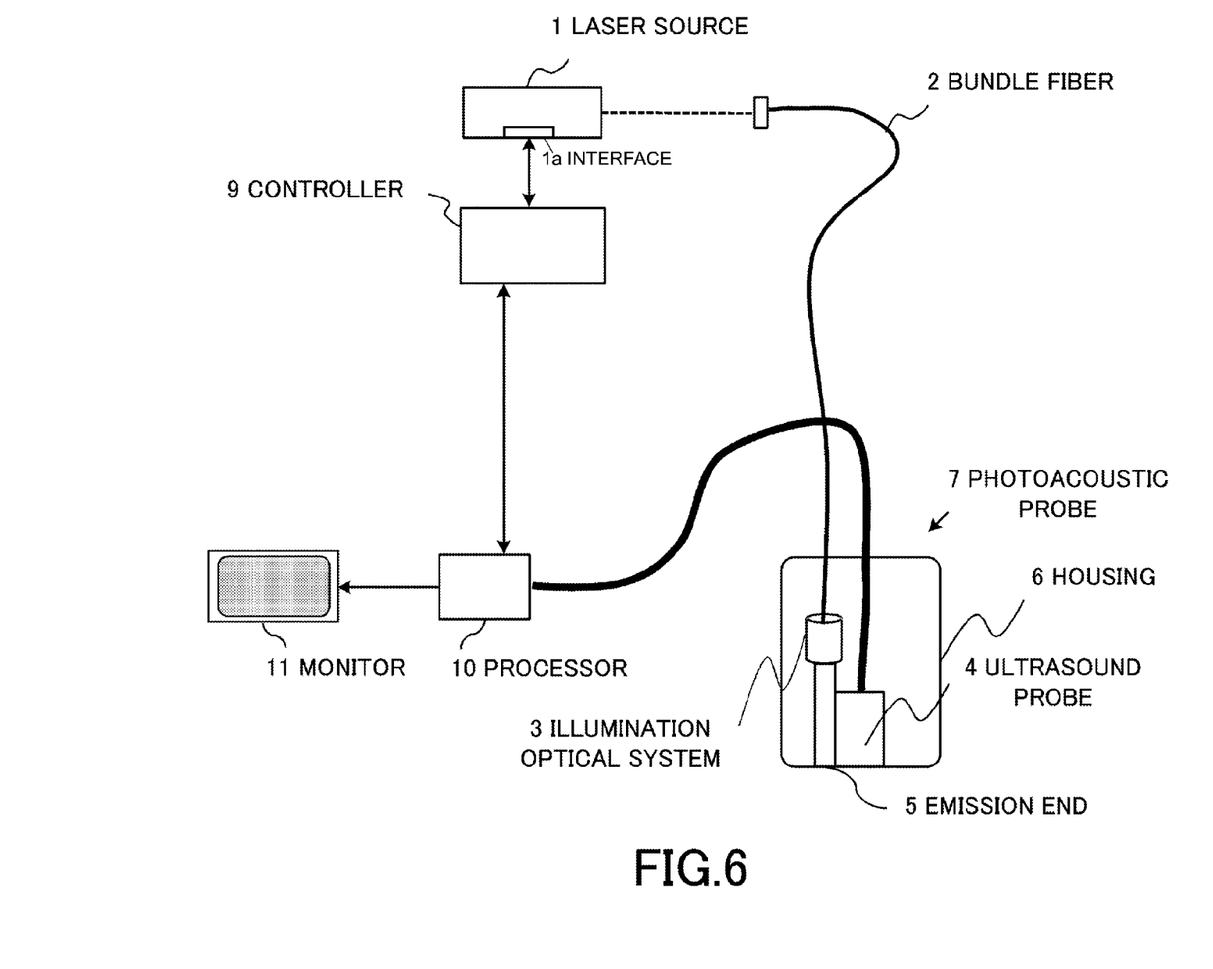
FIG. 6 is a configuration diagram of a photoacoustic measurement apparatus according to a fourth embodiment.

A fourth embodiment is an embodiment where a controller 9 controls a laser source 1 and stops emission of a laser beam in place of arrangement of an emission light limitation unit 8. FIG. 6 shows a system configuration diagram of a photoacoustic measurement apparatus according to the fourth embodiment. A process flowchart of the photoacoustic measurement apparatus according to the fourth embodiment is similar to that of the first embodiment.

In the fourth embodiment, in Step S11 and Step S16, a controller 9 stops issuing, to the laser source 1, a trigger signal for lamp irradiation. When the issuance of the trigger signal is stopped, a lamp necessary for laser excitation does not light, and therefore the emission of a laser beam and the irradiation to an object stop. Then, when the completion of switching of the wavelength is detected, the issuance of the trigger signal of the lamp irradiation to the laser source 1 resumes in Step S14 or Step S19.

In this embodiment, the emission of the laser beam stops without any mechanical components, and therefore the irradiation of the laser beam to the object can be suppressed.

In this embodiment, the emission of the laser beam stops by the stop of the issuance of the trigger signal. However, as long as the light emission of the laser beam can be stopped, other method can be used. For example, a method of causing a QSW signal not to be issued may be employed. Additionally, in a case where a control signal or a control command for suppressing light emission is defined, the signal or the control command maybe issued.

(Modification)

The description of each of the embodiments is merely exemplified for explanation of the present invention, and the present invention can be implemented by appropriate change or combination without departing the spirit of the invention. The present invention can be implemented as a method of controlling an object information acquiring apparatus including at least a part of the aforementioned processes, and can be implemented as a program for causing the object information acquiring apparatus to implement these methods. The aforementioned processes and units can be implemented by free combination as long as no technical consistency occurs.

The object described in each of the embodiments is a biological body such as a breast. However, the present invention is applicable for an object information acquiring apparatus, measurement objects of which include various objects other than a biological body.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-230618, filed on Oct. 18, 2012, which is hereby incorporated by reference herein in its entirety.

What is claimed is:

1. An object information acquiring apparatus applying light to an object, receiving an acoustic wave generated inside the object, and acquiring information on an inside of the object on the basis of the acoustic wave, the object information acquiring apparatus comprising:
   a light source configured to selectively emit irradiation light of at least two different wavelengths, which is applied to the object;
   an acoustic wave probe to receive the acoustic wave generated inside the object;
   a processing unit to acquire information on the basis of the acoustic wave;
   a control unit for instructing the light source to implement switching between the wavelengths of the irradiation light;
   an illumination optical system connected to the light source, and guiding the irradiation light to the object; and
   a light irradiation limiting unit for limiting irradiation of the irradiation light, the light irradiation limiting unit being instructed by the control unit to limit irradiation of the irradiation light to the object during a period from when the control unit provides an instruction on wavelength switching of the irradiation light to the light source to when the light source completes the wavelength switching of the irradiation light,
   wherein the light source notifies the control unit that the wavelength switching is completed, and
   wherein before notification by the light source that the wavelength switching is completed, the control unit instructs the light irradiation limiting unit to limit irradiation of the irradiation light to the object.

2. The object information acquiring apparatus according to claim 1, further comprising a probe for manually scanning an object surface, wherein the irradiation light is applied to the object from the probe, and
   an acoustic wave probe is incorporated in the probe and receives the acoustic wave generated inside the object.

3. The object information acquiring apparatus according to claim 1, wherein the light irradiation limiting unit limits irradiation of the irradiation light to the object by means of a light-shielding mechanism arranged on the illumination optical system.

4. The object information acquiring apparatus according to claim 3, wherein the light-shielding mechanism is a shutter configured to shield the irradiation light.

5. The object information acquiring apparatus according to claim 3, wherein the light-shielding mechanism is a filter configured to attenuate the irradiation light.

6. The object information acquiring apparatus according to claim 3, wherein the light-shielding mechanism is a diffuser panel or a diffusion lens configured to diffuse the irradiation light.

7. The object information acquiring apparatus according to claim 3, wherein the light-shielding mechanism comprises a moving mechanism to move a shielding member onto an optical path of the irradiation light.

8. The object information acquiring apparatus according to claim 1, wherein the light source generates near-infrared rays.

9. The object information acquiring apparatus according to claim 1, wherein the at least two different wavelengths selectively emitted by the irradiation light source are both wavelengths of rays in a range of 400 nm to 1600 nm.

10. The object information acquiring apparatus according to claim 9, wherein the at least two different wavelengths selectively emitted by the irradiation light source are both wavelengths of rays in a range of 700 nm to 1100 nm.

11. The object information acquiring apparatus according to claim 1, wherein the light source comprises a plurality of light sources.

12. The object information acquiring apparatus according to claim 1, wherein the light source includes an interface by which the control unit instructs the light source to implement switching between the wavelengths of the irradiation light and by which the light source notifies the control unit that the wavelength switching is completed.

13. The object information acquiring apparatus according to claim 12, wherein the light source includes a movable wavelength varying mechanism responsive to instruction by the control unit to switch between the wavelengths of the irradiation light, and wherein the light source notifies the control unit via the interface that the wavelength switching is completed based on position of the movable wavelength varying mechanism.

14. The object information acquiring apparatus according to claim 13, wherein the movable wavelength varying mechanism is selected from the group consisting of a birefringent filter and a prism.

15. The object information acquiring apparatus according to claim 1, wherein the light irradiation limiting unit includes an interface by which the light irradiation limiting unit is instructed by the control unit to limit irradiation of the irradiation light.

* * * * *